United States Patent
Fang et al.

(10) Patent No.: US 8,747,110 B2
(45) Date of Patent: Jun. 10, 2014

(54) ORTHOGNATHIC PLANNING SYSTEM AND METHOD

(75) Inventors: Jing-Jing Fang, Tainan (TW); Tung-Yiu Wong, Tainan (TW); Tung-Chin Wu, Kaohsiung (TW); Tai-Hong Kuo, Tainan (TW)

(73) Assignee: National Cheng Kung University, Tainan (TW)

( * ) Notice: Subject to any disclaimer, the term of this patent is extended or adjusted under 35 U.S.C. 154(b) by 151 days.

(21) Appl. No.: 13/543,298

(22) Filed: Jul. 6, 2012

(65) Prior Publication Data
US 2013/0011809 A1 Jan. 10, 2013

(30) Foreign Application Priority Data
Jul. 6, 2011 (TW) .............................. 100123943 A

(51) Int. Cl.
*A61C 11/00* (2006.01)
(52) U.S. Cl.
USPC ................................ 433/54; 433/213; 433/55
(58) Field of Classification Search
USPC .................. 433/54–69, 213–215, 34, 37–38; 382/154, 128, 293, 294; 700/97–98, 700/118; 378/38, 168, 191
See application file for complete search history.

(56) References Cited

U.S. PATENT DOCUMENTS

| | | | | |
|---|---|---|---|---|
| 4,014,097 A | * | 3/1977 | Pameijer | 433/27 |
| 4,354,836 A | * | 10/1982 | Santoni | 433/43 |
| 6,120,290 A | * | 9/2000 | Fukushima et al. | 433/69 |
| 2008/0176182 A1 | | 7/2008 | Hultgren et al. | |
| 2009/0179986 A1 | * | 7/2009 | Klett | 348/77 |
| 2010/0075274 A1 | * | 3/2010 | Klett | 433/56 |
| 2010/0151409 A1 | | 6/2010 | Munehiro | |

* cited by examiner

*Primary Examiner* — Yogesh Patel
(74) *Attorney, Agent, or Firm* — Muncy, Geissler, Olds & Lowe, P.C.

(57) ABSTRACT

An orthognathic planning system applied with at least a dental cast includes an articulator, a detecting device, at least a label module and a data processing device. The dental cast is mounted on the articulator. The detecting device is disposed with respect to the articulator. The label module has at least a label and is disposed on the dental cast. The data processing device is signally connected with the detecting device and stores midface and mandible image data. The detecting device traces the label and provides position data, and the data processing device provides orthognathic planning data in accordance with the position data and the midface and mandible image data. The present invention also discloses an orthognathic planning method.

28 Claims, 12 Drawing Sheets

ORTHOGNATHIC PLANNING SYSTEM AND METHOD

CROSS REFERENCE TO RELATED APPLICATIONS

This Non-provisional application claims priority under 35 U.S.C. §119(a) on Patent Application No(s). 100123943 filed in Taiwan, Republic of China on Jul. 6, 2011, the entire contents of which are hereby incorporated by reference.

BACKGROUND OF THE INVENTION

1. Field of Invention

The invention relates to an orthognathic planning system with a navigation function, and an orthognathic planning method.

2. Related Art

Clinically, there are many patients having special maxillofacial ratios or incorrect occlusal relationships between upper and lower rows of teeth. Such a kind of abnormally growth problem often accompanies with the facial asymmetry, the mandibular prognathism, the mandible retrusion or the poor occlusal condition on the organization structure. Regarding the life, the patient tends to encounter the stoppages, such as the pronunciation difficulties, the chewing digestive diseases, the lack of confidence, or even the other's discrimination and the people's strange looks.

In view of the above-mentioned problems, the general and effective treatment is to correct the spatial positions of the maxilla and mandible through the surgery and to reconstruct the good occlusal relationship. This kind of surgery is typically referred to as an orthognathic surgery. Because the object of the orthognathic surgery is to correct the upper facial structure of the jaw, such as the facial asymmetry, the facial harmonious proportion or the like, as well as the growth problem, or to correct the skeleton structure change, which cannot be easily or cannot be completed using braces. So, the detailed preoperative diagnosis has to be made such that the orthognathic surgery planning can be established in connection with the actual situation of the patient's maxillofacial skeleton structure, and the jawbone can be indeed moved to the proper position. Thus, this is referred to as the "orthognathic surgical planning", "orthognathic planning" or "orthognathic surgery planning", the quality of which significantly affects the quality of the surgical behavior.

In the past, when the orthognathic planning is performed, the doctor only relies on the cephalometric data on the photographed X-ray films of the front side and the lateral side of the patient's head, and then plans the postoperative jawbone position on the articulator. Because only the two-dimensional information is provided by the X-ray images of the front side and the lateral side, but a series of complicated processes including simulating the surgical osteotomy and manufacturing, moving the dental cast and the like have to be performed, the long-term problem that the orthognathic planning on the clinical practice has to rely on the experience and the technique of the main surgeon is caused. When the treatment is not smooth, or even the facial jaw is still slightly skewed although the patient's teeth have the precise occlusal relationships after the surgery, the satisfaction of the orthognathic surgery is affected.

To sum up, the generally existing problems of the conventional orthognathic planning can be generalized as follows. First, the lack of the planning synchronization between the teeth and the jawbone causes the perfect postoperative dentition occlusion but the unsymmetrical overview of the maxilla and the mandible. Second, it is too time-consumptive to perform the adjustment of transferring the cephalometric data to the physical plaster dental cast by way of try-and-error, and the occlusion and symmetry cannot be satisfied concurrently. Third, it is difficult to use the two-dimensional data to truly represent the three-dimensional spatial relationship between the midface and the mandible. Fourth, it is difficult for the orthognathic planning surgery program, mainly based on the occlusion with the aid of the X-ray cephalometric data, to achieve the overall symmetry of the facial jawbone.

Therefore, it is an important subject to provide an orthognathic planning system and an orthognathic planning method, which provide the operator the more precise data, especially the three-dimensional visible data, in the preoperative planning processes, so that the simulation result is closer to the real situation and assists the operator or doctor to achieve the preferred surgical planning target. In addition to avoiding the unnecessary consumption of the labor and time in the try-and-error processes, it is desired to be further advantageous to the reduction of errors, and the enhancement of the orthognathic surgical success rate.

SUMMARY OF THE INVENTION

In view of the foregoing subject, an objective of the invention is to provide an orthognathic planning system and an orthognathic planning method, which provide the operator the more precise data, especially the three-dimensional visible data, in the preoperative planning processes, so that the simulation result is closer to the real situation and assists the operator or doctor to achieve the preferred surgical planning target. In addition to avoiding the unnecessary consumption of the man power and time in the try-and-error processes, the invention is further advantageous to the reduction of errors, and the enhancement of the orthognathic surgical success rate.

Another objective of the invention is to provide an orthognathic planning system and an orthognathic planning method, which can real-time represent or even record the relative position relationship between the dental cast and the craniofacial jaw when moving the dental cast, thereby allowing the operator or doctor to perform comparison and selection among various planning programs. In addition, since the invention can provide the quantitative data, the invention is adapted to the usage in conjunction with the computing software so that the optimum symmetrical surface calculation and the three-dimensional cephalometric analysis can be performed to represent the predicted postoperative result, and assist the operator or doctor in overcoming the blind spots in the three-dimensional space.

To achieve the above objectives, the present invention discloses an orthognathic planning system applied with at least a dental cast. The orthognathic planning system includes an articulator, a detecting device, at least a label module and a data processing device. The dental cast is mounted on the articulator, and the detecting device is disposed with respect to the articulator. The label module has at least a label and is disposed on the dental cast. The data processing device is signally connected with the detecting device and stores midface and mandible image data. The detecting device traces the label and provides position data, and the data processing device provides orthognathic planning data in accordance with the position data and the midface and mandible image data.

To achieve the above objective, the present invention also discloses an orthognathic planning method applied with an orthognathic planning system and a dental cast. The orthognathic planning system includes an articulator, a detecting device, at least a label module and a data processing device. The detecting device is disposed with respect to the articulator. The label module has at least a label and is disposed on the dental cast. The data processing device is signally connected with the detecting device and stores midface and mandible image data. The orthognathic planning method includes the following steps of: mounting the dental cast on the articulator; disposing the label module with respect to the dental cast; utilizing the detecting device to trace the label and provide position data; and utilizing the data processing device to provide orthognathic planning data in accordance with the position data and the midface and mandible image data.

As mentioned hereinabove, the orthognathic planning system and method of the invention utilize the detecting device to trace the labels and to immediately trace the position of the dental cast in the three-dimensional space, and combine the midface and mandible image data, obtained in advance, so that the spatial displacement of the dental cast performed in accordance with the cephalometric planning can synchronously correspond to the facial jawbone image model contained in the midface and mandible image data and become the orthognathic planning data. Because the obtained orthognathic planning data is suitable for the three-dimensional representation, the operator or doctor can perform the stereoscopic observation to advantageously judge the postoperative symmetry, balance the conventional problem of the emphasized occlusion, and sufficiently evaluate whether the content of the orthognathic planning satisfies the surgery target requirement, or whether the adjustment has to be done again. Thus, the orthognathic surgery can achieve the better effects satisfying the functional occlusion and the facial jawbone symmetry.

Compared with the conventional art, the orthognathic planning data provided in accordance with the invention can have the image model representation of the three-dimensional spatial relationship. The invention eliminates the conventional problem, in which the operator or doctor only can perform the evaluation in accordance with the two-dimensional data of the X-ray photo that cannot properly express the spatial relationship of the patient's facial jawbone, and the number of misjudgement or try-and-error conditions is increased. The invention can effectively shorten the planning time and save the manpower. Meanwhile, in the point of view of the preferred target of orthognathic planning (i.e., satisfying the occlusion function and the beauty of symmetry), the orthognathic planning system and method of the invention can visualize the predicted orthognathic result so that the operator can make the intuitive judgement. Most important of all, the orthognathic result can be converted into data, which is suitable for the record and storage or can be used in conjunction with the computing software. The subsequent process, such as the optimum symmetrical plane calculation or the three-dimensional cephalometric analysis, can be performed so that the operator or doctor can make the comparison between various sets of orthognathic planning data, and select and specify the more perfect and careful surgical planning.

BRIEF DESCRIPTION OF THE DRAWINGS

The invention will become more fully understood from the detailed description and accompanying drawings, which are given for illustration only, and thus are not limitative of the present invention, and wherein.

DETAILED DESCRIPTION OF THE INVENTION

The present invention will be apparent from the following detailed description, which proceeds with reference to the accompanying drawings, wherein the same references relate to the same elements.

Figure 1A:
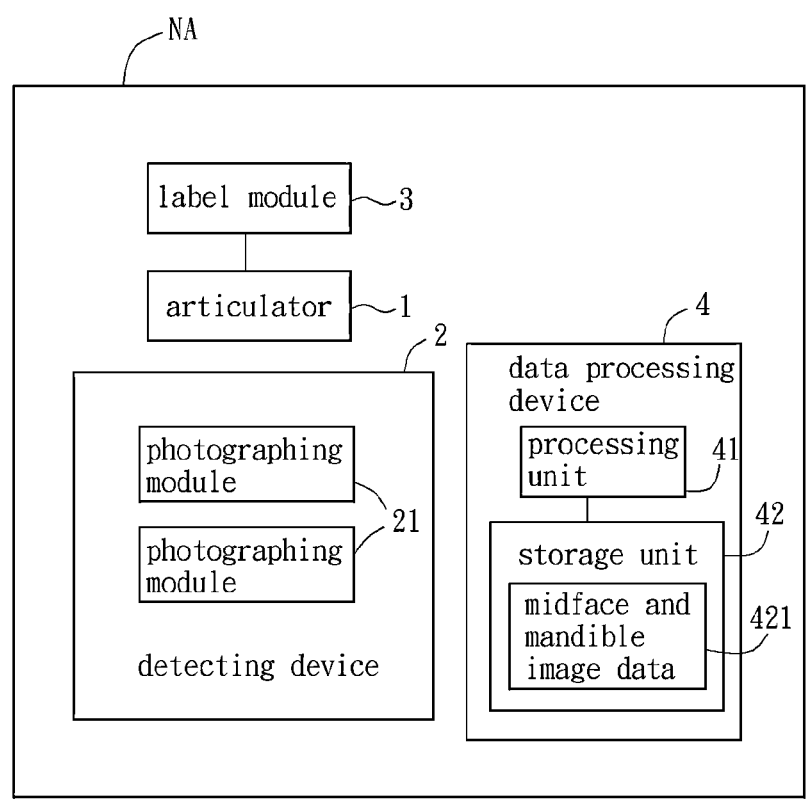
FIG. 1A is a system block diagram showing an orthognathic planning system in accordance with an embodiment of the invention.
Figure 1B:
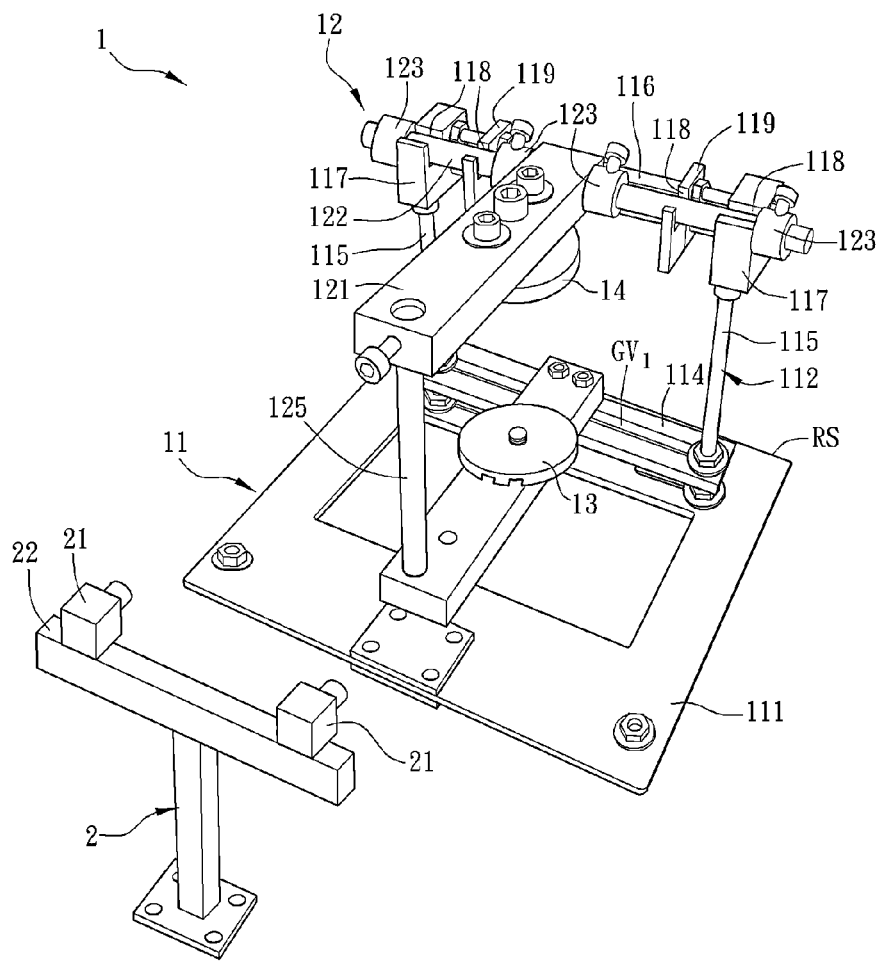
FIG. 1B is a schematic illustration showing an exterior of the orthognathic planning system of FIG. 1A.

In order to perform the preoperative planning properly, the orthognathic planning system of the invention has the specific hardware structure. In the following, the technique characteristics on the hardware will be described, and then the operation method of the orthognathic planning system and the obtained results will be introduced representively in conjunction with one example. FIG. 1A is a system block diagram showing an orthognathic planning system in accordance with an embodiment of the invention, and FIG. 1B is a schematic illustration showing an exterior of the orthognathic planning system of FIG. 1A. Referring to FIG. 1A, an orthognathic planning system NA of this embodiment includes an articulator 1, a detecting device 2, at least a label module 3 and a data processing device 4. The orthognathic planning system NA is applied with at least a dental cast (not shown). However, the numbers of the dental cast is determined in accordance with the predicted result of the orthognathic surgery. Therefore, the orthognathic planning system NA is preferably applied with two dental casts (i.e., a palate dental cast and a mandible dental cast) concurrently, and this embodiment will be continued according to this condition.

As shown in FIG. 1B, the type of the detecting device 2 is not particularly restricted as long as it can detect or sense the label module 3. For example, the detecting device 2 may be an optical, mechanical, ultrasonic, gyroscope or magnetic inductive detecting device or any other detecting device capable of tracing the movement. Of course, different types of detecting devices should work in conjunction with different types of label modules 3. In this embodiment to be described, the detecting device 2 works in conjunction with the active optical technique and has two photographing modules 21, wherein the two photographing modules 21 are disposed on a support structure 22 of the detecting device 2. Preferably, the photographing modules 21 may include, for example but without limitation to, cameras with infrared photographing functions, and the photographing modules 21 have been calibrated and obtained and adjusted the internal parameters and the external parameters. The calibrated photographing module 21 can be used to calculate the stereoscopic visual depth and thus obtains the spatial positioning information of the to-be-tested object. The calibration operation can be easily understood by those skilled in the art and thus will not be described in detail. Although the support structure 22 of this embodiment has the T-shaped frame, it may also have any other arbitrary shape as long as it can fix and maintain the photographing module 21 at the specific position.

Figure 2A:
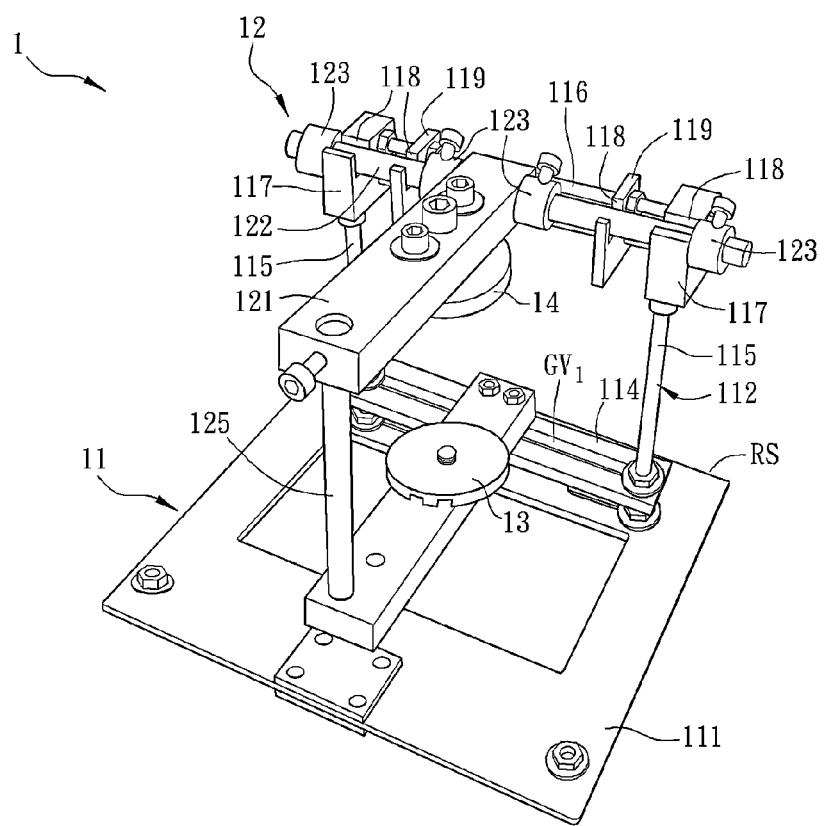
FIG. 2A is a schematic illustration showing an exterior of an articulator in accordance with the embodiment of the invention.
Figure 2B:
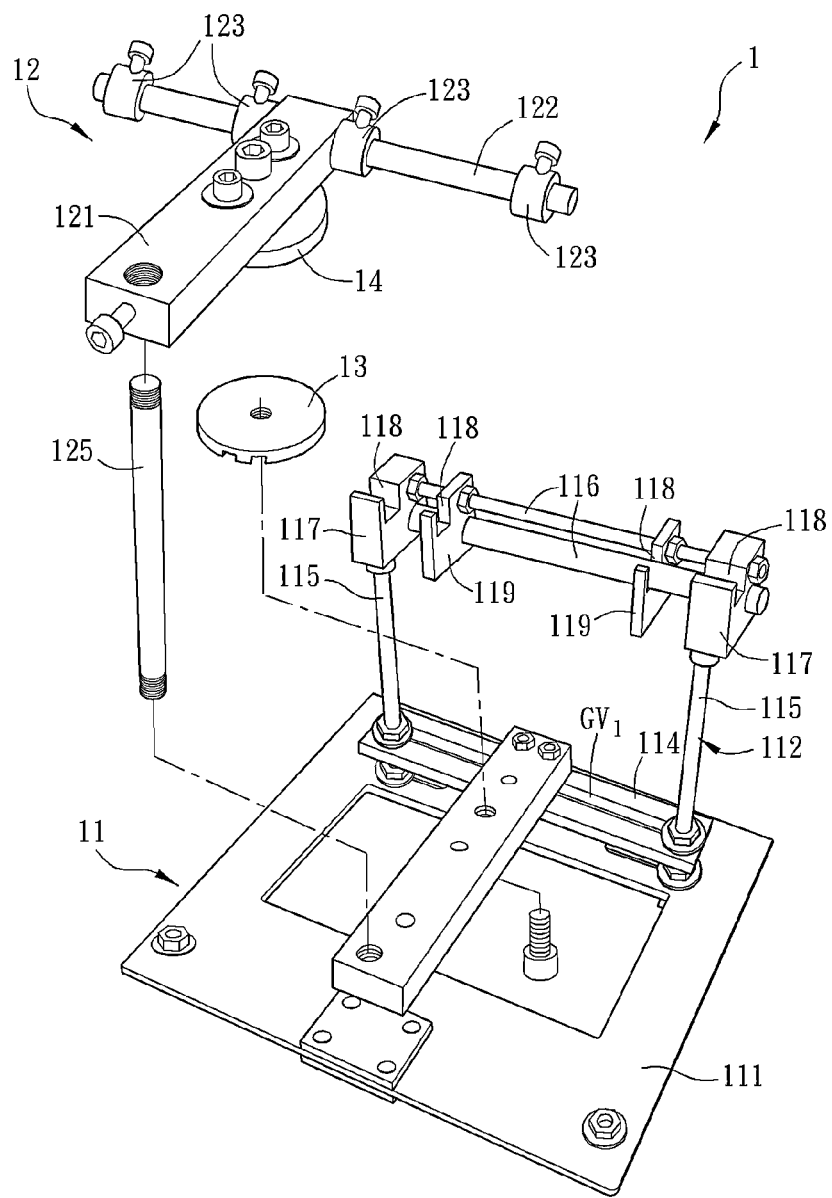
FIG. 2B is an exploded schematic illustration showing the articulator of FIG. 2A.

The detecting device 2 is disposed in correspondence with the articulator 1, and it is preferred that the articulator 1 can be located within the photographing range of the photographing module 21. The articulator 1 of this invention has the structure, which is not particularly restricted, and may be the typical general or conventional articulator 1, but may also be the articulator 1 with the specific structure to be introduced hereinbelow. FIG. 2A is a schematic illustration showing an exterior of an articulator in accordance with the embodiment of the invention, and FIG. 2B is an exploded schematic illustration showing the articulator of FIG. 2A. Referring to FIGS. 2A and 2B concurrently, the articulator 1 of this embodiment has a lower member 11 and an upper member 12, which is detachably mounted on the lower member 11.

Figure 3A:
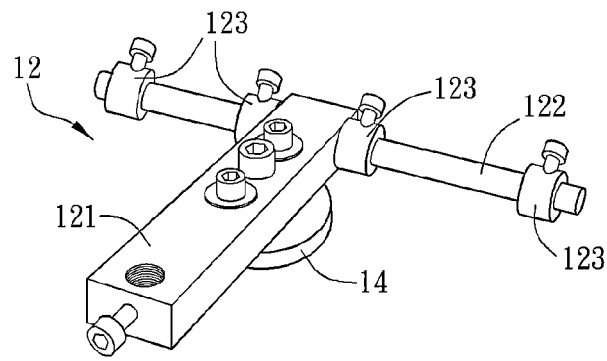
FIG. 3A is a schematic enlarged illustration showing the exterior of the upper member of FIG. 2A.
Figure 3B:
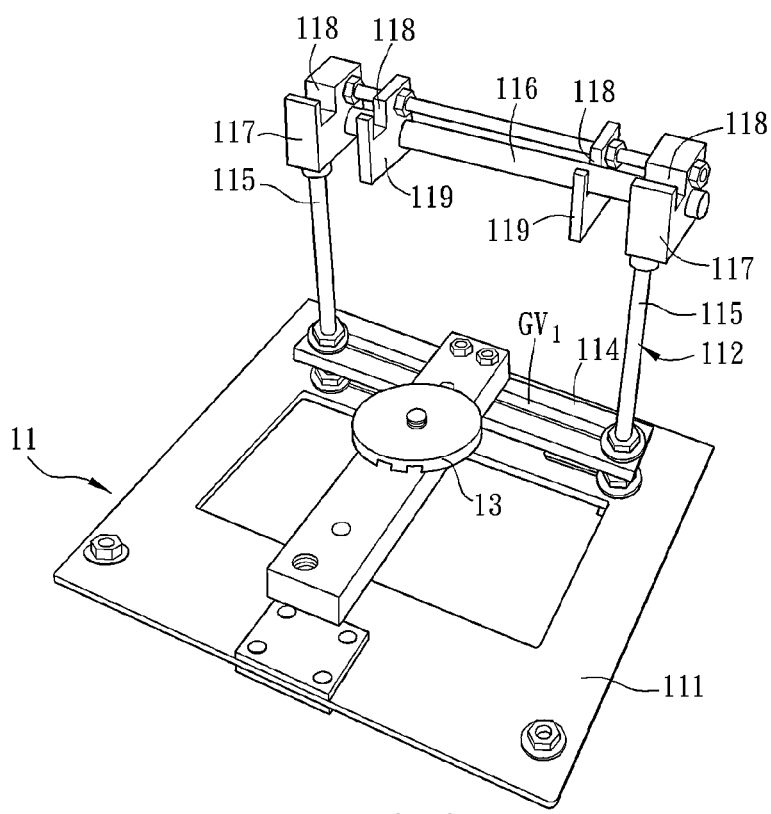
FIG. 3B is a schematic enlarged illustration showing the exterior of the lower member of FIG. 2A.

In the following, the detailed structures of the lower member 11 and the upper member 12 will be further described. FIGS. 3A and 3B are schematic enlarged illustrations showing the exteriors of the upper member and the lower member of FIG. 2A. Firstly, the lower member will be described. Referring to FIG. 3B, the lower member 11 of this embodiment has a base body 111, a frame structure 112 and a lower arm portion 113. The material of each assembly of the lower member 11 may include, for example but without limitation to, metal, and preferably includes carbon fiber, wherein the assemblies have the corresponding screw holes so that they can be fixed and connected together by way of screwing. In this embodiment, the lower arm portion 113 is slidingly disposed on the base body 111. In detail, the rear side RS of the base body 111 may have a fixing platen 114 having a lower arm portion groove $GV_1$ for one end of the lower arm portion 113 to be slidably disposed on. Of course, the lower arm portion groove $GV_1$ may penetrate through the base body, or may be an opening formed on only one side of the base body, and this does not intend to restrict the invention.

The frame structure 112 stands on the rear side RS of the base body 111, and may be further divided into two support columns 115 and two fixing rods 116. In this embodiment, the support column 115 of the frame structure 112 penetrates through two ends of the lower arm portion groove $GV_1$ and is vertically fixed to the base body 111, and one end of each support column 115 corresponding to the base body 111 has an upper fixing member 117. The upper fixing member 117 has a slot 118 having, for example, a U-shape to engage with the upper member 12 and provide the support. The two fixing rods 116 correspond to each other vertically, are disposed between the two upper fixing members 117, and may be fixedly disposed in a condition of, for example but without limitation to, penetrating through the two upper fixing members 117. In addition, in other aspects of this embodiment, the frame structure 112 may also have only one fixing rod 116 disposed between the two upper fixing members 117.

The articulator may have, for example but without limitation to, two position indicators 119 movably disposed on two sides of the frame structure 112 of the lower member 11. Preferably, the position indicators 119 indicate the corresponding relative position relationship between the left and right condyles of the patient, and may be additionally referred to as condyle indicators. For the detailed structures, the position indicator 119 is disposed between the two upper fixing members 117. The position indicator 119 may be a plate-like member having a hole through which the fixing rod 116 passes. Similar to the upper fixing member 117, the position indicator 119 may also have the U-shaped slot 118 for supporting the upper member 12. Of course, the two position indicators 119 are not restricted to be moved concurrently. For example, only one position indicator 119 disposed on one side is movable, and the other position indicator 119 disposed on the other side is fixed and the position of the other position indicator 119 cannot be adjusted.

FIG. 3A is a schematic enlarged illustration showing the exterior of the upper member of FIG. 2A. Referring to FIG. 3A, the upper member 12 has an upper arm portion 121 and a pivot shaft 122 connected with one end of the upper arm portion 121. Preferably, as shown in the drawing, the pivot shaft 122 is connected with the upper arm portion 121 in a manner penetrating through one end of the upper arm portion 121. Preferably, the pivot shaft 122 and the upper arm portion 121 are substantially located on the same plane and correspond to the Frankfurt horizontal plane (hereinafter referred to as the FH plane) of the patient. The pivot shaft 122 may be a cylinder rotatably mounted on the frame structure 112 of the lower member 11. Specifically, it has the shape and the inner diameter matching with the slot 118 of the upper fixing member 117, so that it can be indeed engaged with the upper fixing member 117 without being arbitrarily rotated under the over interference. The assemblies of the upper member 12 may be made of metal, and are preferably made of carbon fiber, and are fixed together by way of screwing.

Referring to again to FIG. 3A, a plurality of positioning members 123 may be fit with the pivot shaft 122 to fix the relative positions between the upper arm portion 121, the pivot shaft 122 and/or the frame structure 112, respectively. In addition, the articulator may also have a rod-like fixing member 125 (see FIG. 2B), which has one end connected with the upper arm portion 121 and the other end connected with the lower arm portion 113.

The articulator is used for accommodating the dental cast of the patient or the person requiring the orthognathic surgery, so a lower alignment member 13 and an upper alignment member 14 corresponding to each other are disposed on the lower arm portion 113 and the upper arm portion 121 of the articulator. In the practical application of this embodiment, the lower alignment member 13 and the upper alignment member 14 may be firstly embedded into the back sides of the mandible and palate dental casts (not shown) corresponding to the teeth occlusal surface, and then the fixing screws are provided to firmly fix the lower alignment member 13 and the upper alignment member 14 to the corresponding surfaces of the lower arm portion 113 and the upper arm portion 121. However, the invention does not intend to restrict the necessity of disposing the dental casts through the lower alignment member 13 and the upper alignment member 14, or the necessity of disposing the lower alignment member 13 and the upper alignment member 14 using the above-mentioned means or order.

Figure 3C:
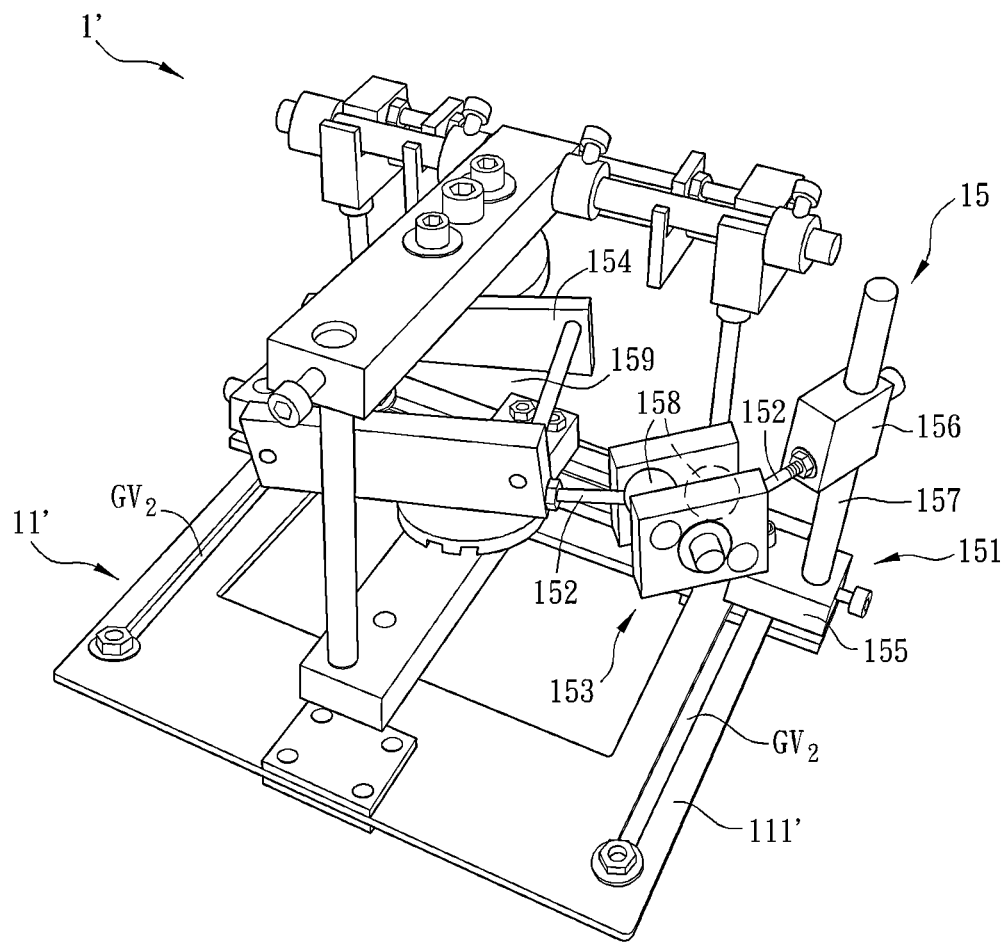
FIG. 3C is a schematic illustration showing the exterior of an articulator in accordance with a modified aspect of the embodiment of the invention.

In addition, when the operator or doctor is cutting and moving the dental cast on the articulator, the material such as the soft wax is required to provide the auxiliary fixing, thereby requiring the repeated softening and fixing steps, and having the poor economic effectiveness in operation. Thus, in addition to the above-mentioned advantages, the articulator of the invention in this aspect is also adapted to the working in conjunction with any structure whose orientation or position can be adjusted, such as a universal arm, especially a hydraulic oil universal arm, so that the above-mentioned problems can be solved. However, it is to be specified that the articulator of the invention may also work in conjunction with a novel approach to serve as another means for solving the similar problems. The approach will be described in the following. However, it is to be emphasized that the novel structure does not intend to restrict the invention. FIG. 3C is a schematic illustration showing the exterior of an articulator in accordance with a modified aspect of the embodiment of the invention. As shown in FIG. 3C, the articulator 1' in this aspect of the embodiment also has elements and the structures of the articulator shown in FIG. 2B, and each of two sides of the base body 111' of the lower member 11' of the articulator 1' further has a dental-cast-adjustment-structure sliding track $GV_2$ for a dental cast adjusting structure 15 to be slidably disposed.

For the detailed structures, the dental cast adjusting structure 15 may have a sliding assembly 151, two links 152, a joint assembly 153 and a dental cast resting assembly 154. The sliding assembly 151 has two block assemblies 155 and 156 and a rod assembly 157, wherein the block assembly 155 is slidingly connected with the dental-cast-adjustment-structure sliding track $GV_2$, and the block assembly 156 is connected with the block assembly 155 in a slidable manner on the rod assembly 157. A dual-sphere joint mechanism mainly constituted by two spheres 158 are disposed on the joint assembly 153, and can provide the rotation in six degrees of freedom. The dental cast resting assembly 154 may be a metal frame having a receptacle 159 for accommodating the dental casts by vertically resting against the dental casts, and directly moving the dental casts upon movement. Links 152 are disposed between the sliding assembly 151, the joint assembly 153 and the dental cast resting assembly 154 to link the assemblies 151, 153 and 154 together. Therefore, the object of fixing or moving the dental casts can be achieved by tightening or loosening the screws of the dental cast adjusting structure 15, thereby eliminating the use of the soft wax and the instability caused by manually moving the dental casts.

Figure 4A:
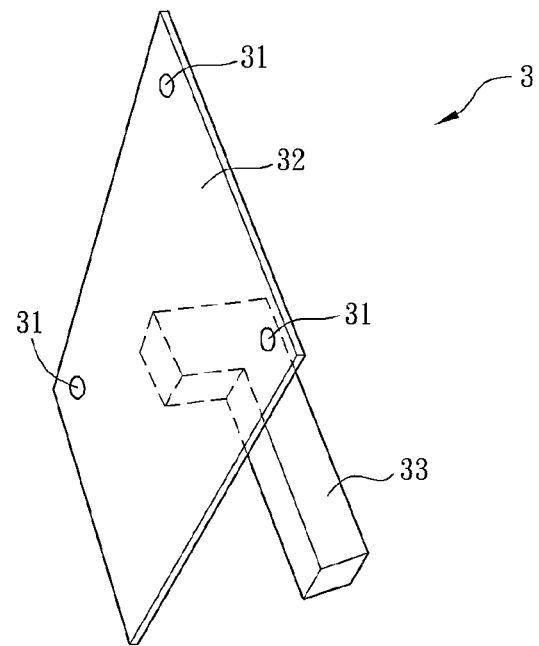
FIG. 4A is a schematic illustration showing the exterior of the label module in accordance with an aspect of the embodiment of the invention.

FIG. 4A is a schematic illustration showing the exterior of the label module in accordance with an aspect of the embodiment of the invention. The label module has at least a label. As shown in FIG. 4A, the label module 3 in this aspect of the embodiment has three labels 31. However, the invention is not restricted thereto. Herein, the use of three labels 31 is only adapted to the active optical technique, and the three labels 31 are used to describe the spatial relationship of six degrees of freedom including three axial moving directions and three rotation directions thereof. Thus, in other embodiments when the detecting device adopts the ultrasonic or magnetic inductive technique, the label module 3 may correspondingly have one label 31.

In this embodiment, the labels 31 are disposed on a label carrying member 32 so that the relative position relationships therebetween can be fixed. In an aspect of this embodiment, the label 31 is a light-emitting diode (LED), preferably an infrared LED, more particularly an infrared LED packaged by way of surface mount technology (SMT). The label carrying member 32 may be a universal printed circuit board (PCB), or a plate material or a sheet material, which generally has wires or can provide the power. The labels 31 are not disposed on the same straight line. As shown in FIG. 4A, the virtual connecting lines between the three labels 31 in this aspect of this embodiment certainly form a triangular serving as the reference of the subsequent calculation. The angles and the lengths of the sides of the triangular are not particularly restricted in this invention. In addition, the back side of the label carrying member 32 may be connected with a connector 33, for example, so that the label module 3 can be connected with other objects, such as the dental cast or an upper arm portion of the articulator. Of course, the connector 33 may be a rod at a fixed angle or a rod that can be arbitrarily rotated.

It is to be specified that, in other embodiment of the invention, if the detecting device adopts the passive tracing technique, then the labels 31 may be replaced with a reflective member or a black-and-white special pattern. However, this does not intend to restrict the invention.

Figure 4B:
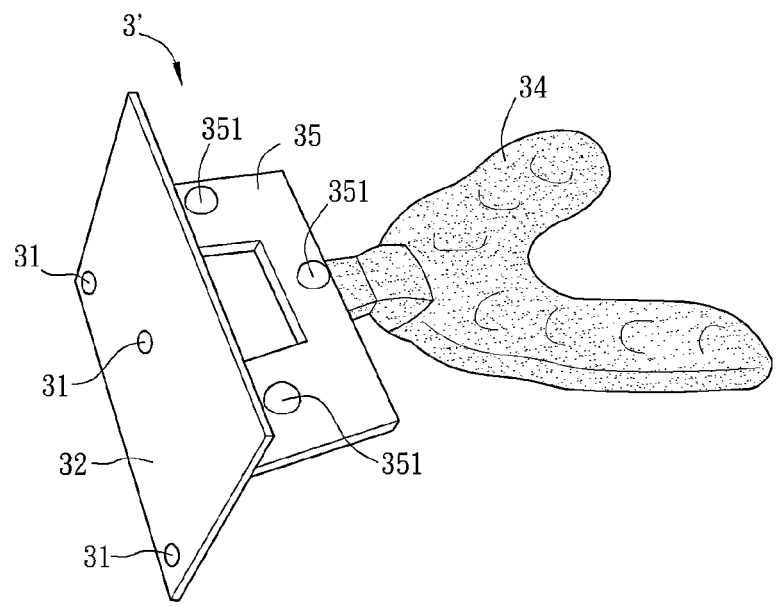
FIG. 4B is a schematic illustration showing the exterior of the label module in accordance with another aspect of the embodiment of the invention.

FIG. 4B is a schematic illustration showing the exterior of the label module in accordance with another aspect of the embodiment of the invention. In order to achieve the effects of the invention preferably and to exactly combine the real position data of the dental cast with the midface and mandible image data, as shown in FIG. 4B, in addition to the element construction and structure in the above-mentioned aspect of the embodiment, the label module 3' in this aspect of this embodiment may further have a bite member 34 and a positioning aid 35. The bite member 34 may be, for example, a bite sheet, a bite stent or the like. The positioning aid 35 may be a plastic sheet that cannot be deformed and has one end connected with the label carrying member 32, and the other end connected with the bite member 34. At least a reference object 351 is disposed on the positioning aid 35 and may include, for example but without limitation to, a ceramic bead or an object, which can be recognized under the X ray, and cannot generate the scattered image during the computed tomography (CT) process, for example. In the aspect of this embodiment, the positioning aid 35 has three reference objects 351, which are not disposed on the same straight line, wherein the virtual connecting lines between the reference objects 351 can form a triangular. When this label module 3' of this aspect is utilized, the patient or the person requiring the orthognathic surgery can bite the bite member 34 before the surgery and the CT is performed. Since the reference objects 351 can be recognized on the CT image and the relative positions between the bite member 34, the reference objects 351 and the labels 31 are fixed, the relative spatial position transforming relationships between the reference objects 351 and the labels 31 can be obtained.

Of course, it is to be emphasized that if the relative spatial position transforming relationships have been obtained or may be established by other methods, then the label module used in this invention does not necessarily possess the elements and structures (i.e., those in the label module 3' of FIG. 4B) in the above-mentioned aspect. In the following, only the orthognathic planning system having at least a label module 3' will be described as an aspect of this embodiment.

Figure 5A:
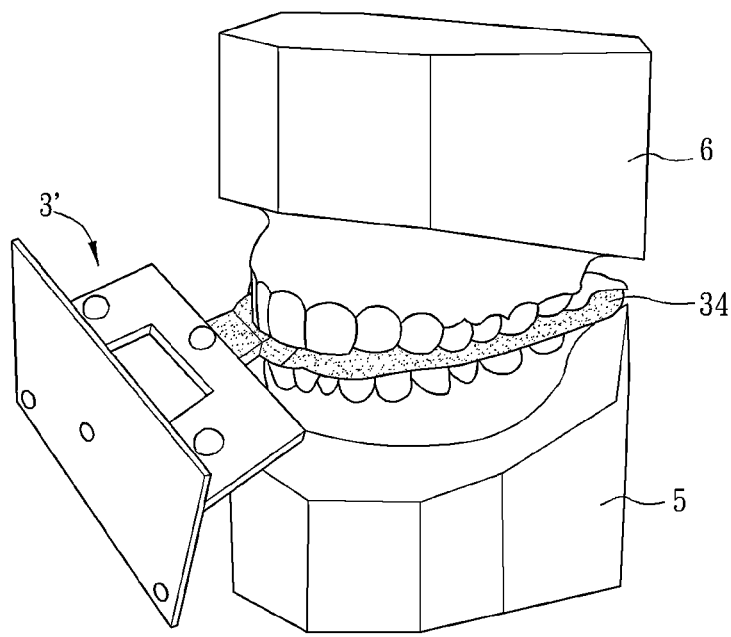
FIG. 5A is a schematic illustration showing a dental cast combined with a label module in accordance with an aspect of the embodiment of the invention.
Figure 5A:
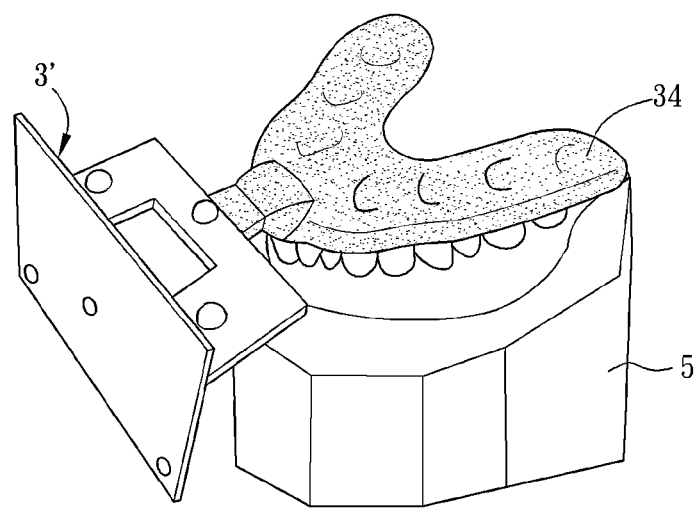
Figure 5B:
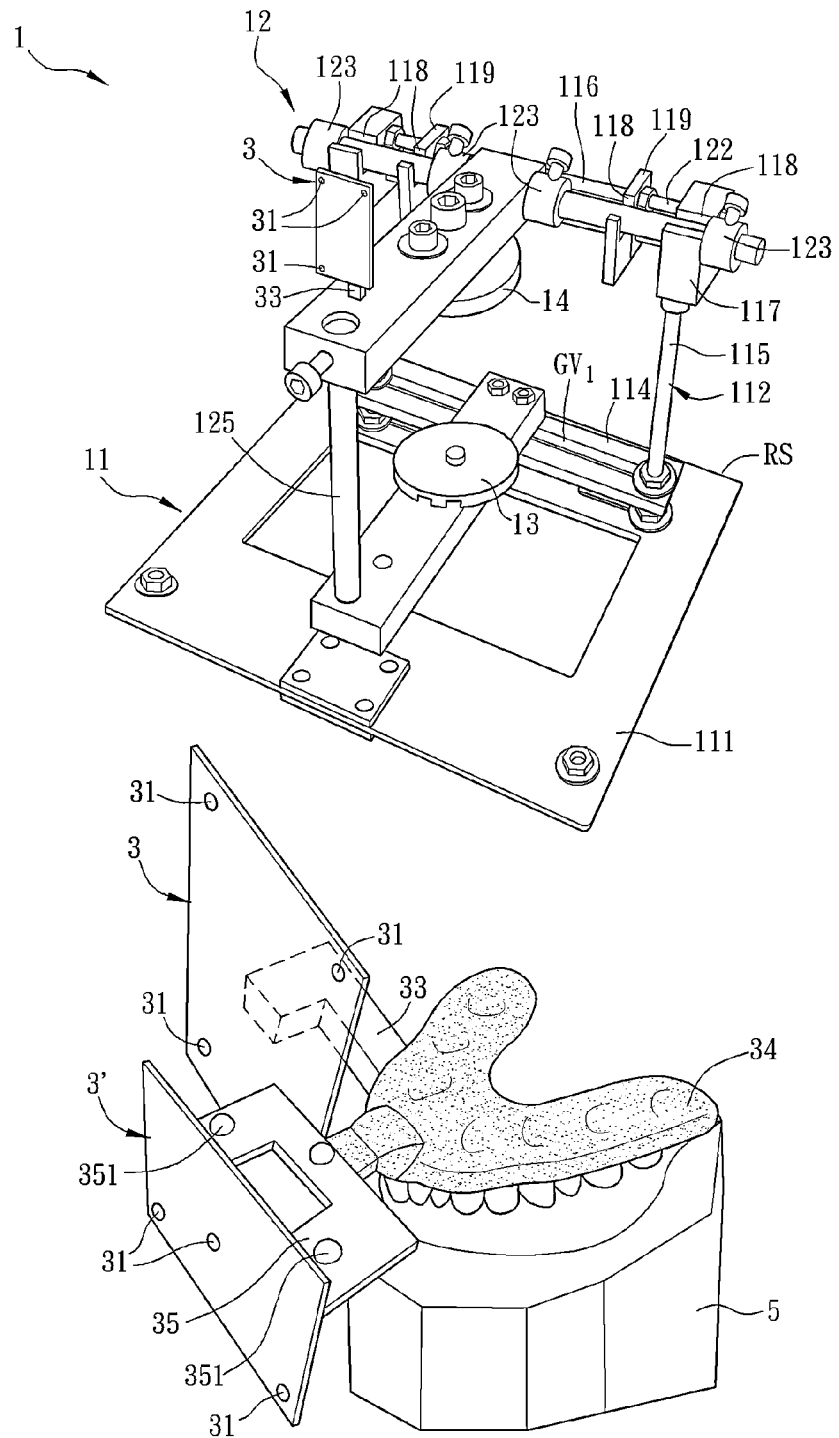
FIG. 5B is a schematic illustration showing the dental cast combined with the label module and the articulator combined with the label module in accordance with another aspect of the embodiment of the invention.

The positions of the label module 3' or 3 shown as FIGS. 4A and 4B will be further described with reference to FIG. 5A. FIG. 5A is a schematic illustration showing a dental cast combined with a label module in accordance with an aspect of the embodiment of the invention. When the orthognathic planning system has one single label module 3', the label module 3' is disposed on the dental cast. For example, the bite member 34 is disposed on a mandible dental cast 5, or a palate dental cast 6 and the mandible dental cast 5 tightly bite the bite member 34. However, it is to be specified that, in addition to the label module 3', whether the label module 3 will be added and how many label modules 3 will be added in practice will be determined in accordance with the arrangement relationships between the devices of the orthognathic planning system and the surgery content. FIG. 5B is a schematic illustration showing the dental cast combined with the label module and the articulator combined with the label module in accordance with another aspect of the embodiment of the invention. As shown in FIG. 5B, in this aspect of the embodiment, the patient needs the mandible osteotomy surgery, the relative position between the detecting device and the articulator 1 is not fixed, and no build-in data is provided for the computing and transforming. Therefore, the orthognathic planning system needs to have one label module 3' and two label modules 3. In addition to tightly fitting with the mandible dental cast 5, the other two are connected with and disposed on the upper side of the upper arm portion 121 and connected with the outer side of the mandible dental cast 5, respectively. It is obtained that if the palate and mandible surgery is to be conducted concurrently, an additional label module 3 needs to be disposed on the palate dental cast (not shown).

As shown in FIG. 1, the data processing device 4 of this embodiment has a processing unit 41 and a storage unit 42. The data processing device 4 is signally connected with the detecting device 2 and stores the midface and mandible image data 421 in the storage unit 42. The midface and mandible image data 421 may include, for example but without limitation to, the image of human teeth, preferably includes the teeth images of the palate and mandible of the human, and more preferably includes the images of the palate and mandible teeth and the facial jawbone. The invention is not particularly restricted thereto. In addition, the data processing device 4 may be signally connected with the detecting device 2 in a wired or wireless manner to receive and process the traced data.

Figure 6:
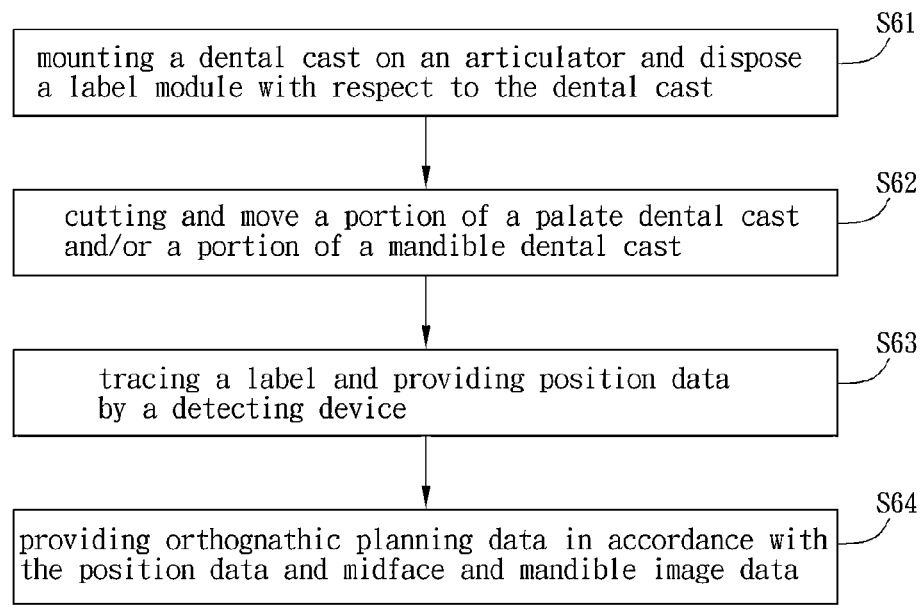
FIG. 6 is a flow chart showing steps of an actual operation when the orthognathic planning system of the embodiment of the invention is applied.

FIG. 6 is a flow chart showing steps of an actual operation when the orthognathic planning system of the embodiment of the invention is applied. The step processes will be described as an embodiment to specifically describe the contents of operating the invention. Referring to FIG. 6 in conjunction with the drawings depicting the details of each device of the orthognathic planning system, the dental cast is firstly mounted on the articulator and the label module is correspondingly disposed on the dental cast in this embodiment, as shown in step S61.

In the above-mentioned step, the dental cast is reproduced from the mouth teeth of the patient or a person requiring the orthognathic surgery (hereinafter collectively referred to as the patient). Preferably, the palate and mandible teeth of the patient are concurrently reproduced into the palate and mandible dental casts, wherein the material of the dental cast includes, for example but without limitation to, the plaster.

In the step S61, mounting the dental cast is performed by an alignment method to mount the palate and mandible dental casts of the patient on the upper and lower alignment members of the articulator with the palate and mandible dental casts of the patient precisely corresponding to the physiological state of the patient. The mounted result is depicted in FIG. 5A.

The alignment method may be mainly classified into two types, one of which utilizes the conventional articulator in conjunction with a face bow, and the other of which is an optical alignment method. The face-bow-type alignment method is well known in the art, and detailed descriptions thereof will be omitted. The optical alignment method may operate in conjunction with the articulator of the embodiment of FIG. 2A, and the detailed steps thereof will be described in the following.

Before the optical alignment, the midface and mandible image data of the patient may be established and stored in advance. In this embodiment, the patient bites the label module 3' having the bite member 34 (see FIG. 4B), and then the CT is performed to obtain and store the midface and mandible image data to the storage unit of the data processing device. Preferably, the midface and mandible image data may represent the image models of the three-dimensional facial jawbone and the maxilla and mandible.

Furthermore, the relative position relationships between the characteristics of the patient can be calculated and recorded as characteristic coordinate data in accordance with the represented result of the midface and mandible image data. The characteristics may include the left and right condyles, upper edges of auditory meatuses of left and right ears, lower edges of orbital bones and/or reference objects 351. Preferably, the left and right condyles are inner points of the left and right condyles. In order to enhance the aligned precision, the articulator may be adjusted in accordance with the relative position relationships between the characteristics before the alignment. For example, as shown in FIG. 2A, the distance between the two position indicators 119 of the articulator 2 may be adjusted to be constant in accordance with the distance between the inner points of the left and right condyles.

In addition to the above-mentioned characteristic coordinate data, the optical alignment method of this embodiment further needs label coordinate data and structure coordinate data. As shown in FIG. 4B, the label coordinate data may be obtained by measuring and recording the coordinate relationships between the reference objects 351 and the labels 31. As shown in FIGS. 2A and 4B, the structure coordinate data is obtained by measuring and recording the relative coordinate relationships between a plurality of structures of the articulator and the labels 31 of the label module 3'. The abovementioned structures may include, for example but without limitation to, the upper arm portion 121, the pivot shaft 122 and/or the two position indicators 119. Preferably, the pivot shaft 122 is a shaft of the upper arm portion 121.

After the three sets of data are obtained, the mandible dental cast is firstly disposed in this embodiment. Please refer to FIGS. 4B and 5A concurrently. First, the label module 3' is correspondingly disposed on the mandible dental cast 5 with the bite member 34 of the label module 3' tightly pressing against the teeth of the mandible dental cast 5, and the status after this process is finished is shown in FIG. 5B. Thereafter, the mandible dental cast 5 mounted with the label module 3' is mounted on the lower alignment member 13, and the detecting device is used to trace the labels 31. The data processing device loads the three sets of data, and displays an image frame on a screen in accordance with the sets of data, for example, so that the operator can adjust the position of the mandible dental cast 5.

In detail, in one aspect of this embodiment, the data processing device is utilized to load the above-mentioned characteristic coordinate data, label coordinate data and structure coordinate data. The characteristic coordinate data includes, for example, the coordinate transfer relationships between the inner points of the left and right condyles and the reference objects 351 in the midface and mandible image data; the structure coordinate data includes, for example, the coordinate transfer relationships between the labels 31 of the label module 3' and the pivot shaft 122 of the articulator 1, the position indicator 119 and the upper arm portion 121, respectively; and the label coordinate data includes, for example, the coordinate transfer relationships between the reference objects 351 of the label module 3' and the labels 31 of the label module 3'.

After the three sets of data are integrated, the image data established by the CT can be combined with the traced results. Accordingly, the relative coordinate position relationship between the mandible image and the articulator 1 can be calculated and shown in FIG. 7A by similarly utilizing the data processing device 4 to load the mandible image data in the midface and mandible image data and combine with the positions of the labels 31 immediately traced by the detecting device.

Figure 7A:
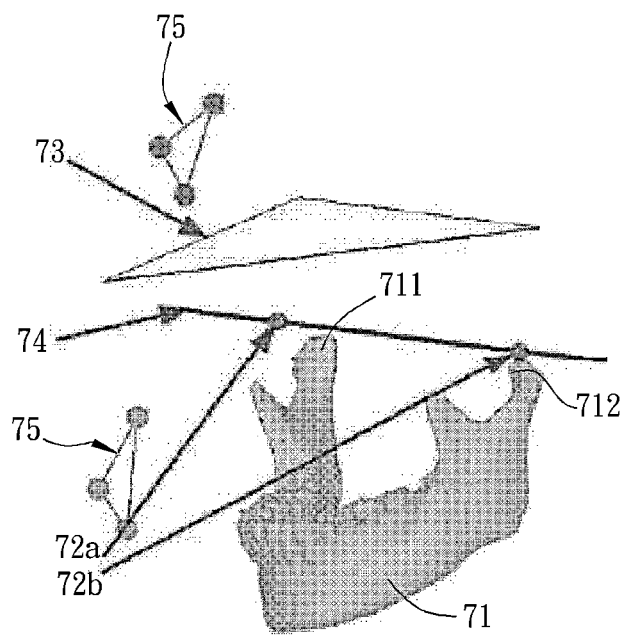
FIG. 7A is a schematic illustration showing an image obtained when the mandible dental cast is aligned in accordance with an aspect of the embodiment of the invention.

FIG. 7A is a schematic illustration showing an image obtained when the mandible dental cast is aligned in accordance with an aspect of the embodiment of the invention. As shown in FIG. 7A, the portions, which are computed by combining the three sets of data with the traced results of the detecting device and then displayed on the frame, may include a mandible image 71, position indicator images 72a and 72b, an upper arm portion image 73, a pivot shaft image 74 and label images 75.

Therefore, the operator or doctor can move the mandible dental cast through the manual or automatic instrument to make condyle inner point images 711 and 712 of the mandible image 71 be overlapped with the positions of the position indicator images 72a and 72b, respectively. After the overlap is completed, it represents that the alignment of the mandible dental cast 5 is completed. Thereafter, the alignment of the palate dental cast can be continued.

Figure 7B:
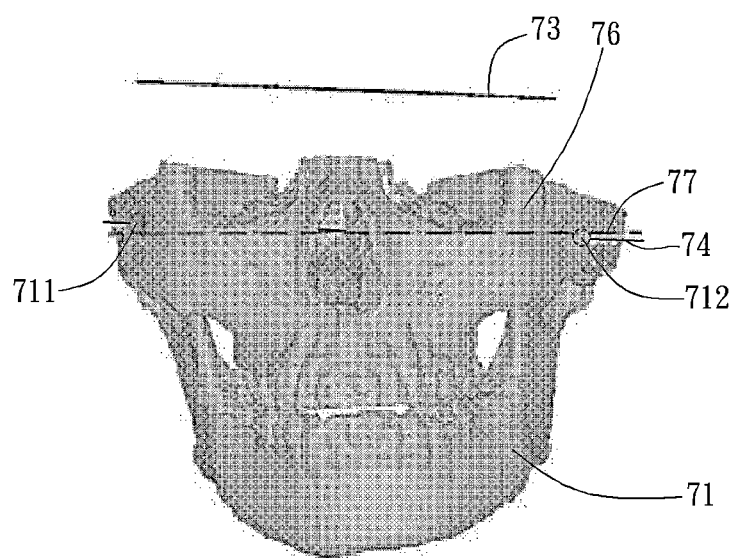
FIG. 7B is a schematic illustration showing an image obtained when the palate dental cast is aligned in accordance with an aspect of the embodiment of the invention.

In the aspect of this embodiment, the label module 3' of FIG. 4B is interposed between the palate dental cast 6 and the mandible dental cast 5, and the result thereof is shown in FIG. 5A. Thereafter, the labels 31 of the label module 3' are similarly traced by the detecting device, and the three sets of data are combined so that the results can be displayed on the frame, as shown in FIG. 7B. Herein, FIG. 7B is a schematic illustration showing an image obtained when the palate dental cast is aligned in accordance with an aspect of the embodiment of the invention. The image contents include the maxilla and at least a portion of maxillofacial bone image 76 of the patient, and the Frankfurt horizontal plane image 77 and the upper arm portion image 73 defined by the data processing device in accordance with the image data. Thus, the operator or doctor can utilize the manual or automatic instrument to rotate the upper arm portion 121 of the articulator 1 until the Frankfurt horizontal plane image 77 is parallel with the upper arm portion image 73, and then fixes the palate dental cast 6 to the upper alignment member 14 to complete the alignment.

It is to be specified that although various articulators have the little structural differences, the alignment method of the invention is constructed based on the tracing technique in conjunction with the three-dimensional imaging technique. Even if the used articulator is different from the structure of the above-mentioned articulator, any combination is still deemed as falling within the scope of the invention as long as the same effect can be achieved.

As shown in FIG. 6 of this embodiment, after the step S61 (after the dental cast has been mounted), the operator or doctor cuts and moves a portion of the palate dental cast and/or a portion of the mandible dental cast (S62) in accordance with, for example, the X-ray cephalometric analysis result of the patient. Preferably, the manual or automatic instrument is used to cut and move the portions of the teeth. The moved palate dental cast and/or mandible dental cast can be further fixed by the soft wax, for example. Of course, in other embodiments where the operator or doctor has completed the cutting and moving of the dental cast before the dental cast is disposed, then the step S62 is not essentially to be performed.

In step S63, the detecting device traces the labels and provides position data. In detail, as shown in FIGS. 4A and 4B, the labels 31 of the label module 3 or the label module 3' can be connected to the teeth portion of the palate dental cast 6 and/or the mandible dental cast 5, so its spatial coordinates are inevitably changed after the movement of the step S62. Therefore, utilizing the detecting device to trace the label 31 in this embodiment can provide the position data, obtained after the dental cast is adjusted in accordance with the X-ray cephalometric analysis, so that the data processing device can perform the subsequent process. Specifically, the position data may include, for example, the position of the label 31 in the spatial coordinate serving as the basis for calculating the positions of the other characteristics after the dental cast is cut and moved.

After the step S63, the data processing device provides orthognathic planning data in accordance with the position data, provided by the detecting device, and the obtained midface and mandible image data, as shown in step S64. Because the orthognathic planning system may alternatively perform an independent step to obtain multiple sets of data containing the label coordinates, the characteristic coordinates and the structure coordinates in the process of aligning the dental cast, the position relationships between the characteristic, articulator structure and label coordinates in the midface and mandible image data can be synthetically calculated. Thus, the positions of the patient's characteristics after movement can be calculated according to the positions of the moved labels, traced by the detecting device, and the positions can be combined with the dental cast image data and then converted into the image frame displayed on the screen, for example, to serve as the orthognathic planning data for the operator's or doctor's reference. Specifically, the orthognathic planning data may, for example, follow the step to perform the surgical planning. After the palate and mandible dental casts on the articulator are moved, the obtained three-dimensional image data can be used to simulate the symmetry of the maxilla and mandible and the teeth occlusion condition of the patient after the surgery is finished. In addition, because the data may be represented in the form of the three-dimensional image, the operator or doctor can easily and directly evaluate whether this orthognathic planning is suitable with his/her naked eyes. Of course, the software calculation may also be utilized to quantify the symmetry of the maxilla and mandible as the symmetrical data, and the value comparison may be performed indirectly. If the evaluated orthognathic planning can be used, the positioning bite stent for the orthognathic surgery can be manufactured accordingly.

Figure 8A:
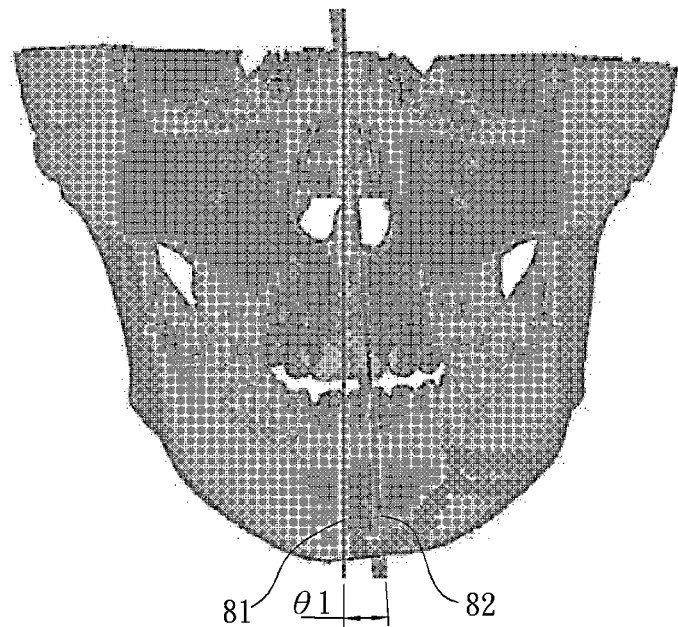
FIGS. 8A and 8B show images of a patient obtained before and after the surgical planning using the orthognathic planning system in accordance with the embodiment of the invention.
Figure 8B:
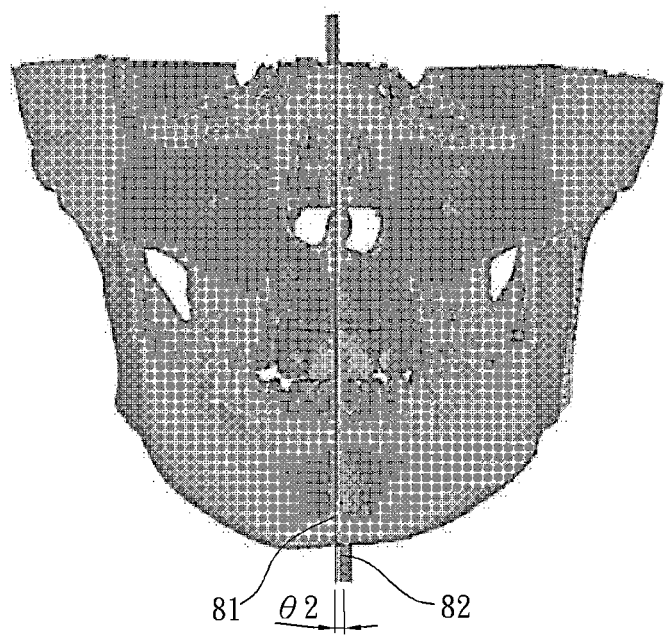

FIGS. 8A and 8B show images of a patient obtained before and after the surgical planning using the orthognathic planning system in accordance with the embodiment of the invention. FIG. 8A represents the patient's CT image before the surgery, and FIG. 8B represents the image of the orthognathic planning data obtained after using the orthognathic planning system of the invention and the corresponding operation procedures to perform the surgical planning to move the palate and mandible dental casts on the articulator. It is clear that, in FIG. 8A, an included angle $\theta 1$ between the plane 81 of palate symmetry and the plane 82 of mandible symmetry is about 4.39 degrees; while in FIG. 8B, the included angle θ2 between the plane 81 of palate symmetry and the plane 82 of mandible symmetry, obtained after moving the dental cast with reference to the X-ray cephalometric planning, is decreased to about 1.67 degrees. Therefore, under the assistant of the three-dimensional image, it is possible to predict that the problem of the skewed mandible of the patient can be indeed improved after the surgery is performed according to this orthognathic planning when either the naked eyes or the data quantifying are utilized.

It is to be specified that the operator or doctor can cut and move the dental cast multiple times in accordance with the orthognathic planning system of the invention to obtain multiple sets of orthognathic planning data and to comprehensively make the comparison and select the optimum surgery program. In addition, since the orthognathic planning system of the invention can perform the real-time tracing, the user or doctor can rotate the upper member, for example, to simulate and synchronously display the change of the included angle between the planes of palate and mandible symmetry in a dynamic tracing manner when the mouth is opened and closed.

The invention additionally discloses an orthognathic planning method applied with an orthognathic planning system and a dental cast. The orthognathic planning system includes an articulator, a detecting device, at least a label module and a data processing device. The detecting device is disposed with respect to the articulator. The label module has at least a label and is disposed on the dental cast. The data processing device is signally connected with the detecting device and stores midface and mandible image data. The orthognathic planning method includes the steps of: mounting the dental cast on the articulator; disposing the label module with respect to the dental cast; utilizing the detecting device to trace the label and provide position data; and utilizing the data processing device to provide orthognathic planning data in accordance with the position data and the midface and mandible image data. However, the step processes, the operation details, the hardware elements and structures in accordance with the orthognathic planning method of the invention are substantially the same as those in the orthognathic planning system and its operation method. Since the descriptions can be found hereinabove, detailed descriptions thereof will be omitted.

In summary, the orthognathic planning system and method of the invention utilize the detecting device to trace the labels and to immediately trace the position of the dental cast in the three-dimensional space, and combine the midface and mandible image data, obtained in advance, so that the spatial displacement of the dental cast performed in accordance with the cephalometric planning can synchronously correspond to the facial jawbone image model contained in the midface and mandible image data and become the orthognathic planning data. Because the obtained orthognathic planning data is suitable for the three-dimensional representation, the operator or doctor can perform the stereoscopic observation to advantageously judge the postoperative symmetry, balance the conventional problem of the emphasized occlusion, and sufficiently evaluate whether the content of the orthognathic planning satisfies the surgery target requirement, or whether the adjustment has to be done again. Thus, the orthognathic surgery can achieve the better effects satisfying the functional occlusion and the facial jawbone symmetry.

Compared with the conventional art, the orthognathic planning data provided in accordance with the invention can have the image model representation of the three-dimensional spatial relationship. The invention eliminates the conventional problem, in which the operator or doctor only can perform the evaluation in accordance with the two-dimensional data of the X-ray photo that cannot properly express the spatial relationship of the patient's facial jawbone, and the number of misjudgement or try-and-error conditions is increased. The invention can effectively shorten the planning time and save the manpower. Meanwhile, in the point of view of the preferred target of orthognathic planning (i.e., satisfying the occlusion function and the beauty of symmetry), the orthognathic planning system and method of the invention can visualize the predicted orthognathic result so that the operator can make the intuitive judgement. Most important of all, the orthognathic result can be converted into data, which is suitable for the record and storage or can be used in conjunction with the computing software. The subsequent process, such as the optimum plane calculation or the three-dimensional cephalometric analysis, can be performed so that the operator or doctor can make the comparison between various sets of orthognathic planning data, and select and specify the more perfect and careful surgical planning.

Although the invention has been described with reference to specific embodiments, this description is not meant to be construed in a limiting sense. Various modifications of the disclosed embodiments, as well as alternative embodiments, will be apparent to persons skilled in the art. It is, therefore, contemplated that the appended claims will cover all modifications that fall within the true scope of the invention.

What is claimed is:

1. An orthognathic planning system applied with at least a dental cast, the orthognathic planning system comprising:
   an articulator, on which the dental cast is mounted;
   a detecting device disposed with respect to the articulator for obtaining a midface and mandible image data;
   at least a label module is disposed on the dental cast, the label module comprising at least a label member, reference objects, a bite member, a positioning aid member and a label carrying member, the positioning aid member has the reference objects, and the positioning aid member is connected with the bite member and the label carrying member, respectively, and the label member is fixed to the label carrying member; and
   a data processing device, which is signally connected with the detecting device and stores midface and mandible image data,
   wherein the detecting device traces the label member and provides position data, and the data processing device provides orthognathic planning data in accordance with the position data and the midface and mandible image data.

2. The system according to claim 1, comprising a plurality of the label modules, and one of the label modules is disposed on the articulator.

3. The system according to claim 1, wherein the articulator has a lower member and an upper member, and the upper member is detachably mounted on the lower member.

4. The system according to claim 3, wherein the lower member has a base body, a frame structure and a lower arm portion, the lower arm portion is slidingly disposed on the base body, and the frame structure stands on the base body.

5. The system according to claim 3, wherein the upper member has an upper arm portion and a pivot shaft, the pivot shaft is connected with one end of the upper arm portion, and the pivot shaft is rotatably mounted on the lower member.

6. The system according to claim 5, wherein the pivot shaft and the upper arm portion are substantially located on the same plane.

7. The system according to claim 3, wherein the articulator has two position indicators movably disposed on two sides of the lower member, respectively.

8. The system according to claim 3, wherein the articulator has a dental cast adjusting structure slidingly disposed on the lower member and resting against a portion of the dental cast.

9. The system according to claim 8, wherein the dental cast adjusting structure has a sliding assembly, two links, a joint assembly and a dental cast resting assembly, and the links connect the sliding assembly, the joint assembly and the dental cast resting assembly together.

10. The system according to claim 9, wherein the joint assembly has two spheres, and the links are connected with the spheres, respectively.

11. The system according to claim 1, wherein the detecting device is an optical, mechanical, ultrasonic, gyroscope or magnetic inductive detecting device.

12. The system according to claim 11, wherein the detecting device is an optical detecting device, and the label is a light-emitting diode (LED), a pattern or a reflective member.

13. The system according to claim 1, wherein the reference objects are not disposed on the same straight line.

14. The system according to claim 1, wherein the label module has a plurality of the label members, and the label members are not disposed on the same straight line.

15. An orthognathic planning method applied with an orthognathic planning system and a dental cast according to claim 1, the orthognathic planning method comprising the steps of:
mounting the dental cast on the articulator;
disposing the label module with respect to the dental cast;
utilizing the detecting device to trace the label member and provide position data;
and utilizing the data processing device to provide orthognathic planning data in accordance with the position data and the midface and mandible image data.

16. The method according to claim 15, wherein the orthognathic planning system comprises a plurality of the label modules, and one of the label modules is disposed on the articulator.

17. The method according to claim 15, wherein the articulator has a lower member and an upper member, and the upper member is detachably mounted on the lower member.

18. The method according to claim 17, wherein the lower member has a base body, a frame structure and a lower arm portion, the lower arm portion is slidingly disposed on the base body, and the frame structure stands on the base body.

19. The method according to claim 17, wherein the upper member has an upper arm portion and a pivot shaft, the pivot shaft is connected with one end of the upper arm portion, and the pivot shaft is rotatably mounted on the lower member.

20. The method according to claim 19, wherein the pivot shaft and the upper arm portion are substantially located on the same plane.

21. The method according to claim 17, wherein the articulator has two position indicators movably disposed on two sides of the lower member, respectively.

22. The method according to claim 17, wherein the articulator has a dental cast adjusting structure slidingly disposed on the lower member and resting against a portion of the dental cast.

23. The method according to claim 22, wherein the dental cast adjusting structure has a sliding assembly, two links, a joint assembly and a dental cast resting assembly, and the links connect the sliding assembly, the joint assembly and the dental cast resting assembly together.

24. The method according to claim 23, wherein the joint assembly has two spheres, and the links are connected with the spheres, respectively.

25. The method according to claim 15, wherein the detecting device is an optical, mechanical, ultrasonic, gyroscope or magnetic inductive detecting device.

26. The method according to claim 25, wherein the detecting device is an optical detecting device, and the label is a light-emitting diode (LED), a pattern or a reflective member.

27. The method according to claim 15, wherein the reference objects are not disposed on the same straight line.

28. The method according to claim 15, wherein the label module has a plurality of the label members, and the label members are not disposed on the same straight line.

* * * * *